(12) United States Patent
Fask et al.

(10) Patent No.: US 6,315,145 B1
(45) Date of Patent: Nov. 13, 2001

(54) LID FOR A SPECIMEN CONTAINER THAT IS ADAPTED TO MINIMIZE SPILLS AND LEAKS

(75) Inventors: Richard J. Fask, Worcester, MA (US); James E. Meegan, Warwick, RI (US); Thomas M. Brindamour, Rehoboth, MA (US); John Drummey, Mansfield, MA (US); Patricia Drummey; Thomas H. Drummey, both of Plainville, MA (US)

(73) Assignee: StickSafe LLC, Mansfield, MA (US)

( * ) Notice: Subject to any disclaimer, the term of this patent is extended or adjusted under 35 U.S.C. 154(b) by 0 days.

(21) Appl. No.: 09/313,864

(22) Filed: May 18, 1999

Related U.S. Application Data

(63) Continuation-in-part of application No. 08/501,815, filed on Jul. 13, 1995, now Pat. No. 5,904,677.

(51) Int. Cl.⁷ .................................................... B65D 51/18
(52) U.S. Cl. .................... 220/254; 215/247; 215/DIG. 3; 604/415
(58) Field of Search ..................................... 215/247, 355, 215/306, DIG. 3; 220/254, 810, 832, 229, DIG. 19, 256, 255, 789, 375; 604/415; 206/828

(56) References Cited

U.S. PATENT DOCUMENTS

| | | |
|---|---|---|
| 2,142,278 | 1/1939 | Mendelson . |
| 2,364,126 | 12/1944 | Cantor et al. . |
| 2,421,313 * | 5/1947 | Brandon ................................ 215/247 |
| 2,436,291 * | 2/1948 | Daniel ................................ 220/229 X |
| 2,533,165 * | 12/1950 | Hagedorn ............................ 604/415 X |
| 2,585,938 | 2/1952 | Jordan . |
| 2,608,972 | 9/1952 | Chrigstrom . |
| 2,689,562 * | 9/1954 | Adams et al. .................... 604/415 X |
| 2,690,861 * | 10/1954 | Tupper ............................... 220/375 X |
| 3,709,395 * | 1/1973 | Brennan et al. ...................... 215/247 |
| 3,855,997 | 12/1974 | Sauer . |
| 3,881,465 | 5/1975 | Raitto . |
| 3,982,649 * | 9/1976 | Wanderer .................. 220/DIG. 19 X |
| 4,244,920 | 1/1981 | Manschot et al. . |
| 4,254,884 * | 3/1981 | Maruyama ........................ 215/247 X |
| 4,278,437 | 7/1981 | Haggar . |
| 4,327,842 * | 5/1982 | Walter . |
| 4,331,254 * | 5/1982 | Haggerty ............................ 215/247 X |
| 4,356,924 * | 11/1982 | Walter . |
| 4,437,574 * | 3/1984 | Ruklic ..................................... 215/247 |
| 4,576,306 * | 3/1986 | Kelsey et al. ..................... 220/375 X |
| 4,643,825 * | 2/1987 | Weslowski ........................ 220/375 X |
| 4,863,453 | 9/1989 | Berger et al. . |
| 5,061,263 * | 10/1991 | Yamazaki et al. ............... 215/247 X |

(List continued on next page.)

FOREIGN PATENT DOCUMENTS

| | | | |
|---|---|---|---|
| 2701694 * | 8/1994 | (AU) | ................................... 220/229 |
| 338108 * | 6/1959 | (CH) | ................................... 215/306 |
| 2651749 * | 3/1991 | (FR) | ................................... 220/254 |
| IE94/00006 | 9/1994 | (WO) . | |

*Primary Examiner*—Allan N. Shoap
*Assistant Examiner*—Robin A Hylton
(74) *Attorney, Agent, or Firm*—Mirick, O'Connell, DeMallie & Lougee, LLP

(57) ABSTRACT

An improved specimen container comprising a receptacle, a lid having a top surface and a bottom surface and a bore therethrough, and a resealable membrane plug which has an upper and lower annular shoulder, at least one of which shoulders is deformable, and which is inserted through and seated in the bore of the lid so that said upper annular shoulder is seated on the top surface of the lid and the lower annular shoulder is seated on the bottom surface of the lid, and a plug cover which can be raised and lowered by the user with one hand leaving the user's other hand free to insert a specimen into, or withdraw a specimen from, the specimen container.

9 Claims, 27 Drawing Sheets

U.S. PATENT DOCUMENTS

| | | | |
|---|---|---|---|
| 5,088,612 | * 2/1992 | Storar et al. | 215/247 |
| 5,139,492 | 8/1992 | Leise, Jr. et al. | |
| 5,257,984 | 11/1993 | Kelley. | |
| 5,297,561 | 3/1994 | Hulon. | |
| 5,297,599 | * 3/1994 | Bucheli | 215/247 X |
| 5,384,096 | 1/1995 | Burns. | |
| 5,458,854 | 10/1995 | Burns. | |
| 5,482,591 | * 1/1996 | Reo | 215/247 X |
| 5,611,792 | 3/1997 | Gustafsson. | |
| 5,711,306 | * 1/1998 | Guilluy | 215/247 X |
| 5,766,939 | * 6/1998 | Kayal et al. | 220/DIG. 19 X |
| 5,863,791 | * 1/1999 | Baldszun et al. | 220/832 X |
| 5,895,383 | * 4/1999 | Niedospial, Jr. | 604/415 X |
| 5,904,677 | * 5/1999 | Drummey et al. | 604/415 |
| 5,931,828 | * 8/1999 | Durkee | 215/247 X |
| 6,030,582 | * 2/2000 | Levy | 215/247 X |

* cited by examiner

LID FOR A SPECIMEN CONTAINER THAT IS ADAPTED TO MINIMIZE SPILLS AND LEAKS

CROSS-REFERENCE

This is a continuation-in-part of U.S. application Ser. No. 08/501,815 filed on Jul. 13, 1995 now U.S. Pat. No. 5,904,677.

FIELD OF THE INVENTION

This invention relates to an improved specimen container which is adapted to maintain the sterile integrity of the container and to prevent leakage yet which can be temporarily, partially opened and closed with one hand, leaving the other hand free to insert the specimen with a needle and syringe (N&S), cannula and syringe (C&S) or a syringe with no attachment without having to first put the instrument down.

BACKGROUND OF THE INVENTION

Specimen containers are well known in the art and are available in a host of shapes and sizes. However, a user of specimen containers typically must use both hands to operate the container. The user must hold the receptacle in one hand and remove the cover with the other hand, while holding a syringe containing an aspirated specimen. The user must then squirt the specimen into the open receptacle, risking the possibility of splash back or spillage. Therefore, it has been identified that a specimen container which enables a user to grasp, open and close the lid with one hand, and with the user's other hand, to inject the aspirated specimen into the container without splash back or to withdraw a specimen from the container without spillage, would be beneficial to the user. Further, it is also recognized that a specimen container which facilitates insertion of a cannula or a syringe with no attachment into the specimen container by providing a cannula guide would also be beneficial.

SUMMARY OF THE INVENTION

It is therefore a primary object of this invention to provide a specimen container which enables a user to grasp a specimen container with one hand and, with the user's other hand, to inject the aspirated specimen into the container without splash back or to withdraw a specimen from the container without spillage.

It is a further object of this invention to provide a specimen container having a plug cover which enables a user to grasp, open and close the plug cover with one hand, and with the user's other hand, to inject the aspirated specimen into the container without splash back or to withdraw a specimen from the container without spillage.

It is a further object of this invention to provide a specimen container which facilitates insertion of an instrument, such as a needle or cannula, into the specimen container by providing a guide for the tip of the instrument.

It is a further object of this invention to provide a lid, provided with one or more self-resealing portals therethrough, for any type of receptacle adapted to contain a solid and/or a liquid.

A preferred embodiment of the specimen container of this invention, adapted to maintain the sterile integrity of the container and to prevent leakage, comprises: a receptacle having an opening; a lid comprising a means to seal said opening and having a top surface and a bottom surface and a bore therethrough; and a plug comprising, an upper and lower shoulder, at least one of said shoulders is deformable, wherein said plug is seated in said bore of said lid so that said upper shoulder is seated on said top surface of said lid and said lower shoulder is seated on said bottom surface of said lid, and a membrane capable of being penetrated with a material transfer device and which self-reseals to prevent leakage from said container. Material transfer device generally refers to a variety of instruments used to transfer fluids or other similar materials from one point to another, including but not limited to cannulas, needles and syringes connected to a somewhat pointed attachment adapted to puncture a membrane.

The specimen container may further comprise a plug cover, preferably comprising high density polyethylene, which covers a top surface of the plug and which is adapted to be raised and lowered by a person's one hand leaving the person's other hand free to insert a specimen into, or withdraw a specimen from, the specimen container. The plug cover is preferably hingedly fixed to the lid and includes a flange which surrounds the upper shoulder of the plug when in a lowered position. The plug cover may further comprise a flange which is adapted to engage a corresponding flange on the lid when the plug cover is in a lowered position so that the plug cover is removably fixed in the lowered position to further prevent any material from entering or leaking out of the receptacle. A portion of the plug cover preferably extends beyond the outer edge or boundary of the lid. The plug may be adapted to be removed after the plug is inserted through and seated in the bore for purposes of replacement or otherwise.

The shoulders of the preferred embodiment of the specimen container are generally annular and the plug of the specimen container may further comprise an instrument guide for directing the instrument into the plug and through the self-sealing membrane. If such an instrument guide is provided, the guide typically has an outer diameter and the plug should further comprise one or more means for altering the outer diameter of the instrument guide to enable the guide to adaptably flex in order to accommodate instruments such as needles or cannulas having varying outer diameters. The means for altering the outer diameter preferably comprises one or more expandable slits in the plug which extend radially outward from the instrument guide.

In the specimen container of the invention, the upper shoulder preferably has an outer diameter greater than the lower shoulder and the lid may further comprise a conduit, which extends into the receptacle of the container downward from the bottom surface of the lid, through which said bore further extends, and which comprises a lower lip on which the lower shoulder of said plug is seated.

The receptacle typically comprises threads proximate the opening of the receptacle and the means to seal the opening of the receptacle comprises threads on the lid which correspond to threads on the receptacle. The plug of the specimen container may be molded from thermoplastic rubber and may also include a continuous ridge on the top surface of the plug, wherein the ridge presses against an underside of the plug cover to provide additional protection against leakage.

Yet another preferred embodiment of the plug and plug cover of the invention are connected to each other by a flexible cord. The plug, plug cover and flexible cord of this embodiment are preferably a molded unitary member molded from thermoplastic rubber, C-Flex or isoprene.

Yet another preferred embodiment of the improved specimen container of the invention, adapted to enable a user to inject or withdraw materials into or out of said container using a material transfer device with minimal risk of spills or leaks, comprises: a receptacle having an opening; a lid comprising a means to seal said opening and at least a first bore and a second bore therethrough; and a first plug, which is seated in said first bore of said lid comprising, a membrane capable of being penetrated with a material transfer device and which self-reseals to prevent leakage from said receptacle; and a second plug which is seated in said second bore. Said second bore is adapted allow a material transfer device, a syringe without an attachment, a sterile loop and transfer pipet to be inserted at least partially into the specimen container. Both the first and second plug may each be provided with a plug cover. The plug covers may be connected to their respective plugs with or without flexible cords.

Yet another preferred embodiment of the improved specimen container of the invention, adapted to enable a user to inject or withdraw materials into or out of said container using a material transfer device with minimal risk of spills or leaks, comprises: a receptacle having an opening; and a molded lid comprising a bore therethrough and a self-resealable membrane insert-molded into the lid and across the bore.

Yet another preferred embodiment of the improved specimen container, adapted to enable a user to inject or withdraw materials into or out of said container using a material transfer device with minimal risk of spills or leaks, comprises: a receptacle having an opening; and a molded lid, having a top surface, comprising a bore therethrough and a self-resealable membrane fixed to the top surface of the lid and across the bore.

The lid of the invention may be adapted for virtually any type of receptacle for containing a solid or liquid adapted to be covered or otherwise sealed with a lid having one or more limited access portals therethrough. It is envisioned that the lid of the invention may be useful for non-medical uses including but not limited to collecting environmental or industrial specimens for testing, storing and transportation.

BRIEF DESCRIPTION OF THE DRAWINGS

Other objects, features and advantages will occur to those skilled in the art from the following description of the preferred embodiments and the accompanying drawings in which.

DETAILED DESCRIPTION OF THE PREFERRED EMBODIMENTS

The specimen container of the invention, which is adapted to enable a user to grasp the container with one hand and, with the user's other hand, to inject or withdraw a specimen into or out of the sealed container using an instrument such as a syringe or cannula without splash back or spillage and without having to set the instrument down to remove a lid, generally comprises, a specimen receptacle, a lid with a bore through the lid, and a self-sealing, removable plug which fits into and through the bore and can be pierced with the cannula.

Figure 1:
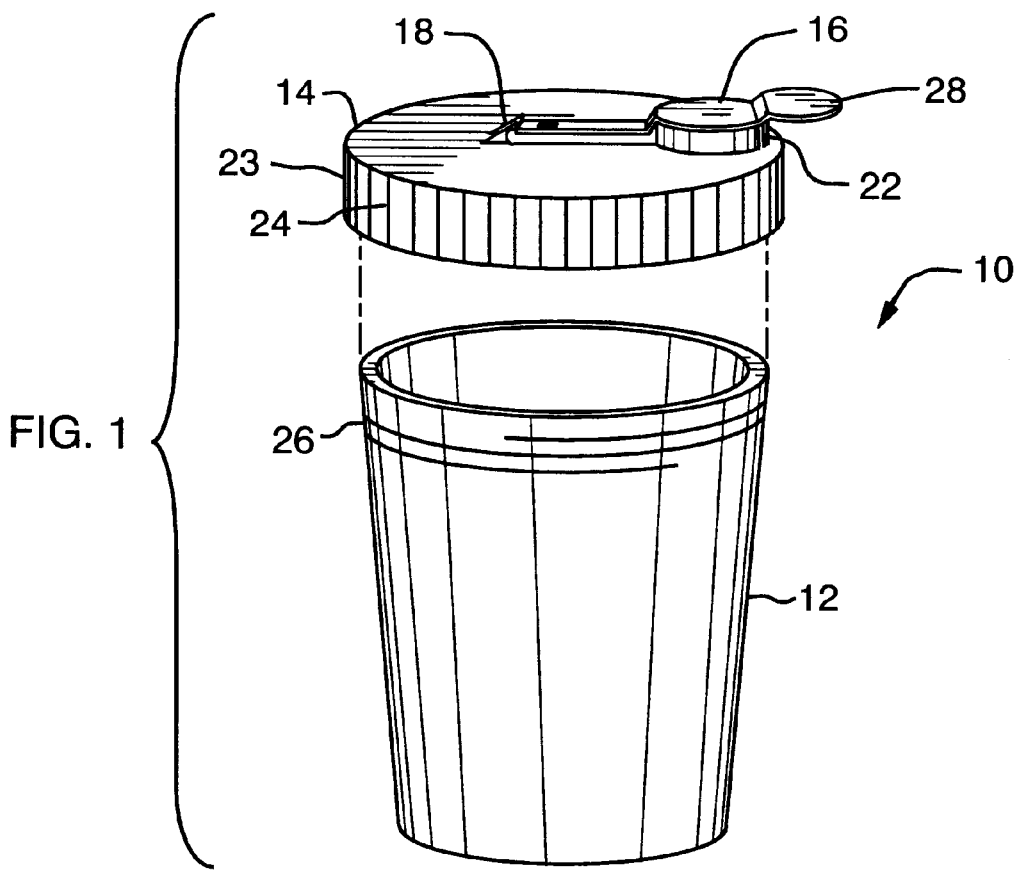
FIG. 1 is an exploded side view of a preferred embodiment of the specimen container of the invention.

A preferred embodiment of the container of this invention is shown and generally referred to in FIG. 1 as container 10. Container 10 generally comprises receptacle 12 and lid 14. Threads 26 are provided on receptacle 12 proximate the lip of receptacle 12 which engage corresponding threads 27 (shown in FIG. 2B) located on the inside of cylindrical wall 23 of lid 14 to positively seal lid 14 from being axially displaced from receptacle 12. Lid 14 is provided with vertical ridges 24 around the outside of cylindrical wall 23, to grip lid 14 while attaching and removing lid 14 to and from receptacle 12, respectively, and sleeve-like bore 25 which extends (shown in FIGS. 2A and 2B) downward through lid 14 and is located off center of lid 14.

As an alternate to threads 26 and 27 as the means for sealing the opening of receptacle 12, lid 14 and receptacle 12 may alternatively be provided with a means for snapping the lid onto the receptacle.

Container 10 is also provided with plug 38 (shown in FIGS. 2B and 4A–4F) which is seated in bore 25 and has a top shoulder and a bottom shoulder which sit on the top surface of lid 14 and the bottom edge of sleeve-like bore 25, respectively. The top of plug 38 is covered by plug cover 16 (shown in FIGS. 1, 2A, 2B and 3A–3I). Plug cover 16 is preferably made of molded high density polyethylene.

Plug cover 16 is provided with cam 20 which removably fixes the cover to lid 14 by hingedly engaging two raised cam locks 18 provided on the top surface of lid 14. Cam 20 snaps into and is frictionally held in cam locks 18. Each one of cam locks 18 (FIG. 2C) has a generally triangular shape from the side, however the top of the triangle is missing to form channel 17. The center of the triangle is also missing to form groove 19. Channel 17 and groove 19 of one of the cam locks should be parallel to channel 17 and groove 19 of the other cam lock. Plug cover 16 is removably fixed to lid 14 by pressing cam 20 into channel 17 until cam 20 locks into place in groove 19. Channel 17 should angle inward slightly down to groove 19 so that the lower end of channel 17 which opens into groove 19 is smaller in width than the largest diameter of groove 19. The diameter of cam 20 should be slightly greater than the lower end of channel 17 and the same as or slightly smaller than the diameter of groove 19.

Figure 10:
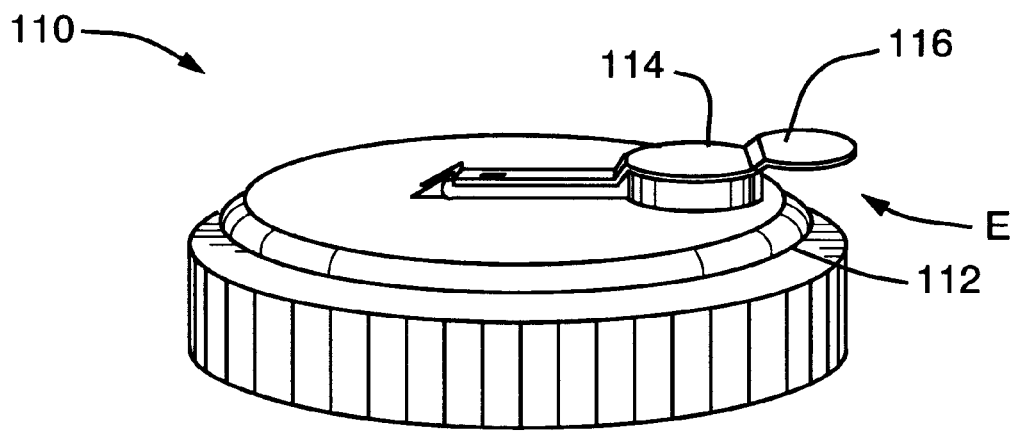
FIG. 10 is a perspective view of another preferred embodiment of the lid of the specimen container of the invention.

Plug cover 16 is also provided with notch 36 (shown in FIGS. 3G and 3H) on flange 34 which engages a corresponding notch located on flange 22 provided on lid 14. Tip portion 28 of plug cover 16 extends partially outward from the periphery of lid 14 to enable the user with one hand to release and raise plug cover 16 from the notch on flange 22 with a flip of the user's thumb or finger. Tip portion 28 should extend beyond the periphery of lid 14 as needed to provide the user sufficient leverage to raise plug cover 16. The periphery of lid 14 may have an inwardly stepped edge (FIG. 10). In FIG. 10, lid 110 is provided with stepped edge 112 so that the user can wedge his or her finger between steps 112 and tip portion 116 of plug cover 114. Utilizing a stepped edge reduces the distance to which tip portion 116 needs to extend beyond the outer periphery of lid 110.

Figure 2B:
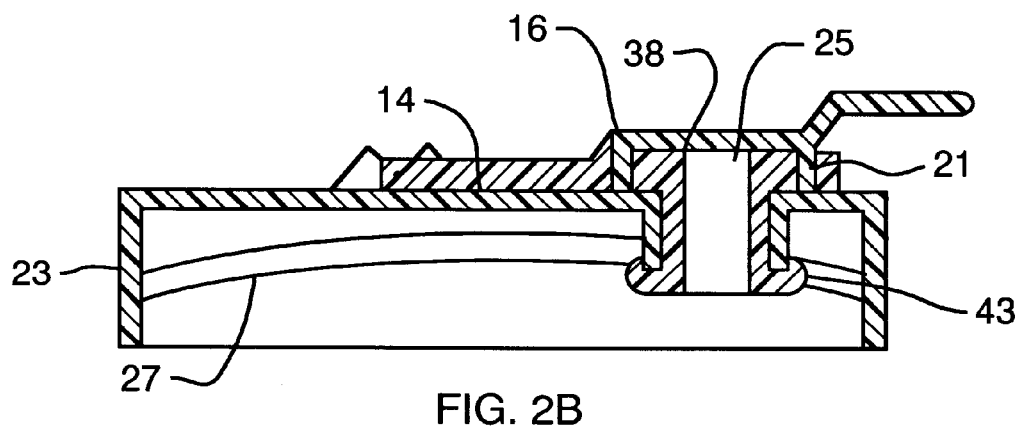
FIG. 2B is a cross-sectional view of the lid of the preferred embodiment shown in FIG. 2A along section "E"—"E"
Figure 3A:
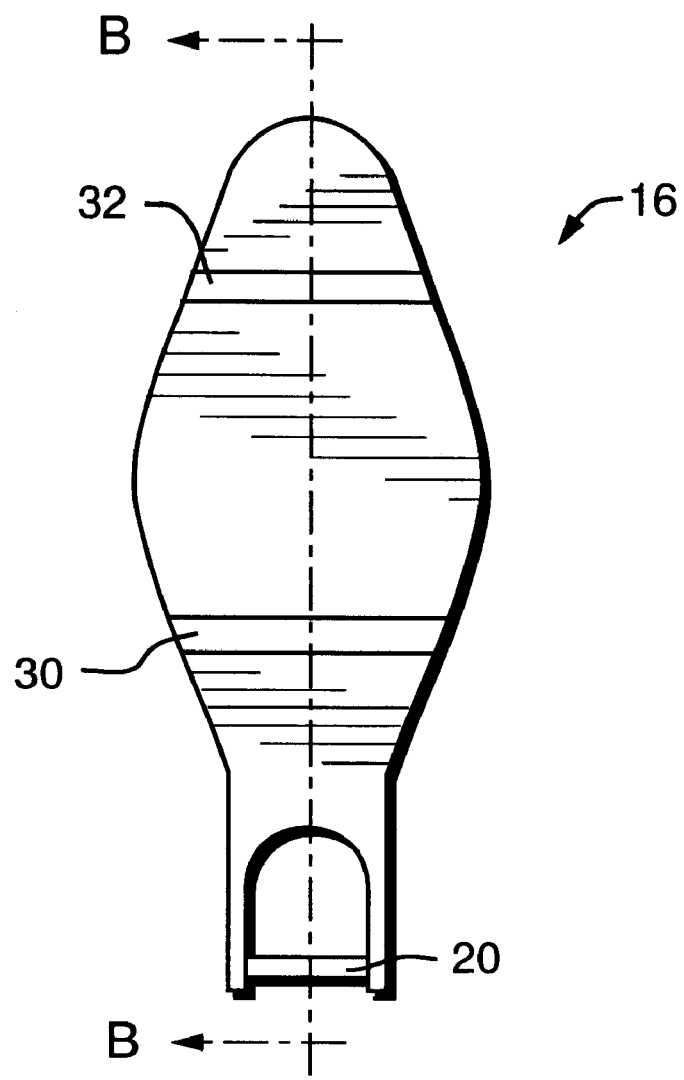
FIG. 3A is a top view of the plug cover of the preferred embodiment shown in FIG. 1.
Figure 3B:
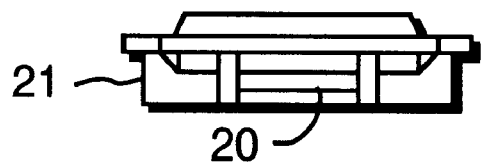
FIG. 3B is a rear view of the plug cover shown in FIG. 3A.
Figure 3C:
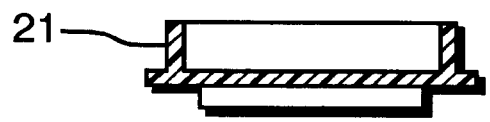
FIG. 3C is a cross-sectional view of the plug cover shown in FIG. 3A along section "A"—"A"
Figure 3D:
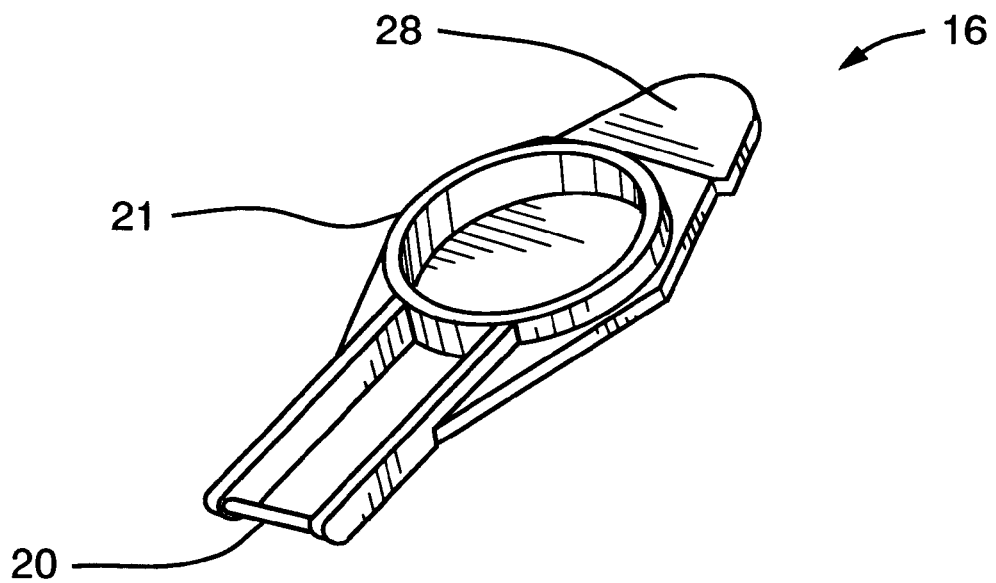
FIG. 3D is a perspective bottom view of the plug cover shown in FIG. 3A.
Figure 3E:
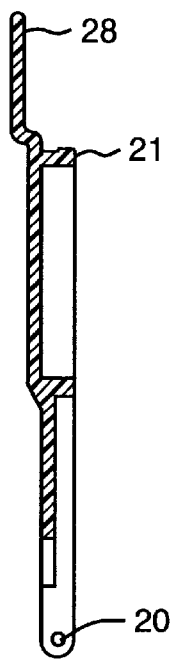
FIG. 3E is a cross-sectional view of the plug cover shown in FIG. 3A along section "B"—"B"
Figure 3F:
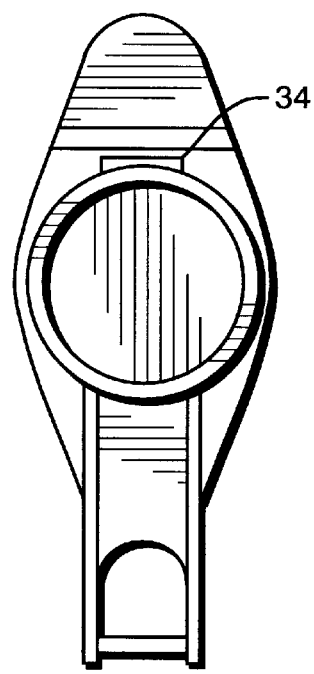
FIG. 3F is a bottom view of the plug cover shown in FIG. 3A.
Figure 3G:
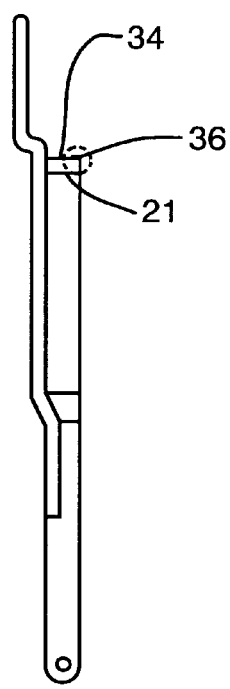
FIG. 3G is a side view of the plug cover shown in FIG. 3A.
Figure 3H:
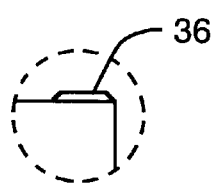
FIG. 3H is an enlarged view of the tab shown in FIG. 3A.
Figure 3I:
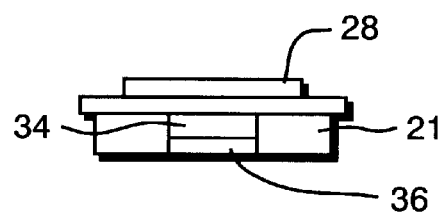
FIG. 3I is a front view of the plug cover shown in FIG. 3A.

Plug cover 16 is portioned into three increasingly stepped sections as shown in FIGS. 3E and 3G. The first and lowest section of plug cover 16 is bounded by cam 20 at one end and rises in elevation to the second and middle section at step 30 (FIG. 3A). Wall 21 extends downward from the bottom surface of plug cover 16 (FIGS. 2B, 3B, 3C, 3D, 3E, 3G and 3I) so that when plug cover 16 engages the notch on flange 22 in a closed position, wall 21 substantially covers and seals the top of plug 38 and bore 25. The middle section of the plug cover rises further in elevation to the third and upper section at step 32 (FIG. 3A). The upper section forms tip portion 28 which extends beyond the periphery of lid 14. Wall 21 should have an inside dimension which is the same as or slightly greater than the corresponding outer dimension of plug 38. In the preferred embodiment, the outer dimension of the upper shoulder of plug 38 is 0.577 inches (FIG. 4C) and the inside dimension of wall 21 is 0.580 inches (FIG. 3E).

Plug cover 16 is also provided with notch 36 (FIGS. 3G and 3H) proximate the lower edge of flange 34. Flange 34 is essentially a thickened and slightly forwardly protruding portion of wall 21 nearest tip portion 28 (FIG. 3F). When plug cover 16 is in a closed position, notch 36 of plug cover 16 engages the notch on flange 22 of lid 14. Notch 36 can be readily released from the notch on flange 22 by lifting gently upward on tip portion 28. Depending on the relative dimensions of the specimen container, notch 36 and the notch on flange 22, when engaged should be small enough to require only minimal pressure to disengage notch 36 from the notch on flange 22. For example, notch 36 of lid 14 is a mere 0.005 inches thick. The notch on flange 22, likewise, corresponds in size to notch 36.

Figure 2A:
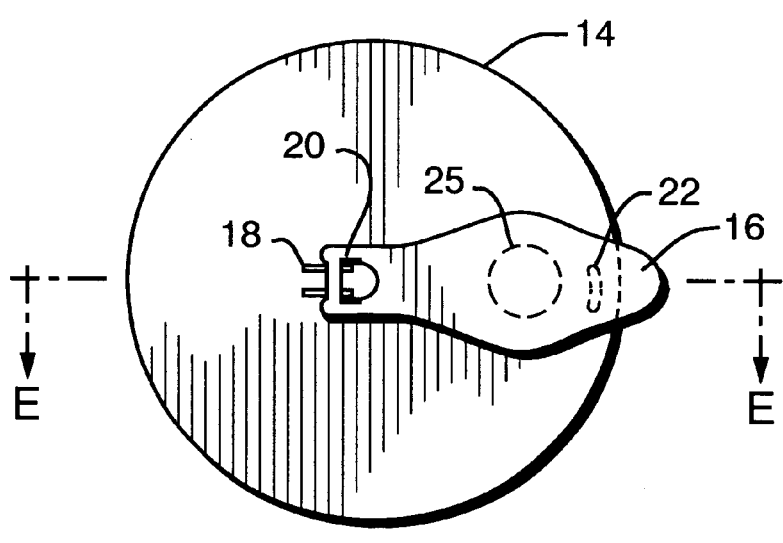
FIG. 2A is a top view of the preferred embodiment shown in FIG. 1.

Flange 22 is not limited to a single notch or a single flange as shown in FIG. 2A but rather may comprise a series of notches or flanges which extend further around the circumference of lid 14. For example, it may be desirable to provide a greater notch area on flange 22 to hold plug cover 16 more securely against lid 14 when plug cover 16 is in a closed position. This object may be achieved by increasing the size of flange 22, and likewise the notch on flange 22, or by providing more than one flange 22 around the perimeter of lid 14, each flange having a notch capable of engaging a corresponding notch on plug cover 16.

Figure 2C:
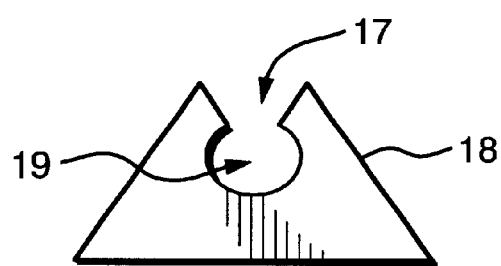
FIG. 2C is an enlarged side view of a groove provided on the lid of the preferred embodiment shown in FIG. 1.
Figure 4B:
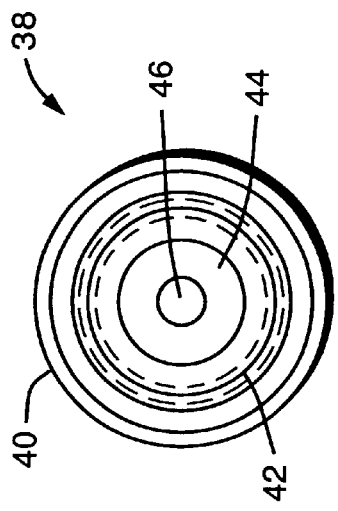
FIG. 4B is a bottom view of the plug shown in FIG. 4A.
Figure 4D:
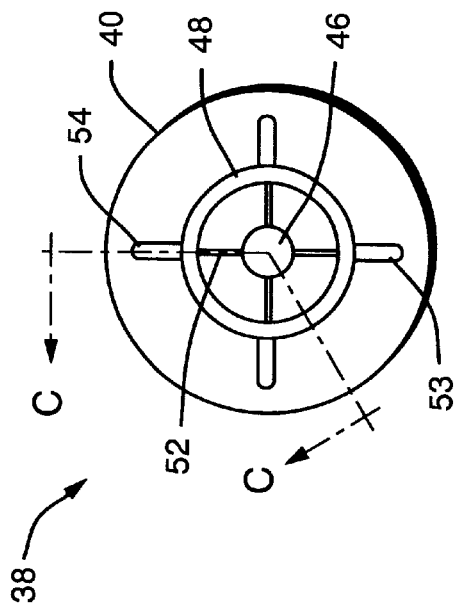
FIG. 4D is a top view of the plug shown in FIG. 4A.
Figure 4A:
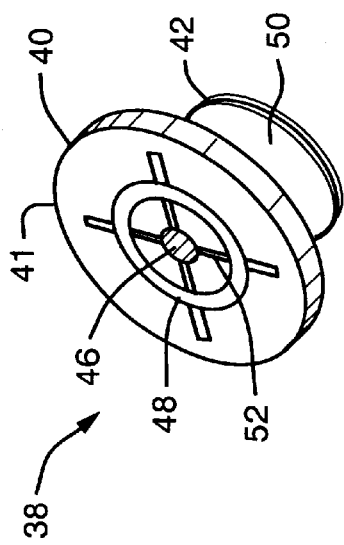
FIG. 4A is a perspective view of the plug of the preferred embodiment shown in FIG. 1.
Figure 4C:
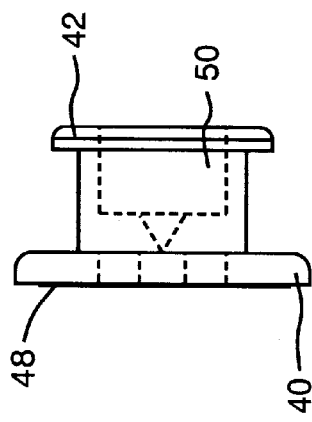
FIG. 4C is a side view of the plug shown in FIG. 4A.
Figure 4E:
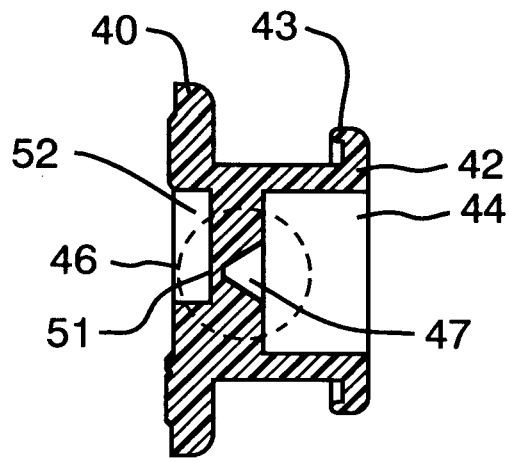
FIG. 4E is a cross-sectional view of the plug shown in FIG. 4A along section "C"—"C" as shown in FIG. 4D.

As noted, container 10 is also provided with plug 38. Plug 38 is preferably made of molded thermoplastic rubber, C-Flex or isoprene. Plug 38 is preferably deformable so that the plug can be inserted into bore 25 for quick and easy assembly. Plug 38 has a larger upper shoulder 40 and a smaller lower shoulder 42, (FIGS. 4A–4C and 4E). When plug 38 is inserted into bore 25, shoulder 40 is seated on the top surface of lid 14 and shoulder 42 is seated on the bottom edge of bore 25, as shown in FIG. 2B. Shoulder 42 preferably has a lip 43 which slightly wraps around the bottom edge of bore 25 to prevent plug 38 from being pulled up through bore 25 as the end of a cannula is pulled out through plug 38 (FIGS. 2B and 4E). Plug 38 has a slightly elongate portion 50 between shoulders 40 and 42 to accommodate the downward extension of sleeve-like bore 25 as shown in FIG. 2B. Elongate portion 50 of plug 38 should be about the same as the internal length of bore 25.

Figure 4F:
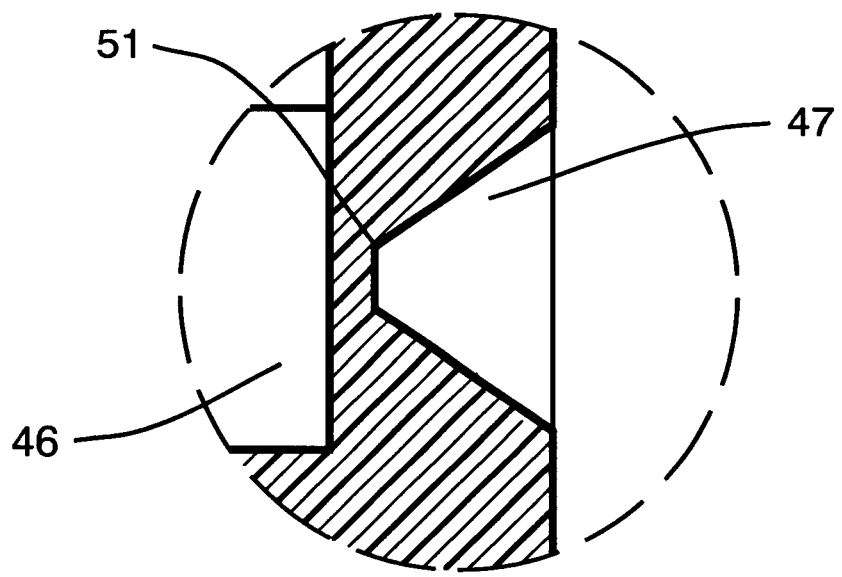
FIG. 4F is an enlarged view of Detail D shown in FIG. 4E.

Plug 38 also has a central bore 44, however bore 44 does not extend the entire length of plug 38 as shown in FIG. 4E. A thin section at the upper end of elongate portion 50 is solid across its diameter to form self-sealing membrane 51. A small inverted notch 47 is provided in the bottom of membrane 51 to guide a material transfer device (not shown) back out through plug 38 and to channel any material back into receptacle 12 (FIG. 4F). The hole created by inserting a transfer device through membrane 51 will effectively close when the transfer device is removed due to the elasticity of thermoplastic rubber, C-Flex or isoprene. The term material transfer device generally refers to any of a variety of instruments having a pointed tip capable of puncturing a membrane and used to transfer fluids or other similar materials from one place to another, including but not limited to cannulas, needles and syringes connected to an attachment having a pointed tip adapted to puncture a membrane.

Upper surface 41 of plug 38 is substantially solid across its face except for transfer device guide 46 and expansion slits 52. Annular sealing ridge 48 also extends upward from upper surface 41 so that when plug cover 16 is closed, sealing ridge 48 presses firmly against the bottom surface of the middle portion of plug cover 16 within cylindrical wall 21 to further inhibit leakage from container 10. Top surface 41 may also include radial ridges 53 (FIG. 4D) to aid the user to line up the tip of the transfer device with the central bore.

The plug of the invention may also be made by a technique known as insert molding. This technique requires shooting heated plug material into a pre-molded housing in the lid. Insert molding would eliminate the need for separate production and installation of the plug.

Transfer device guide 46 is a cylindrical well formed in upper surface 41. Membrane 51 forms the bottom transfer device guide 46. Transfer device guide 46 should have a diameter sufficient to receive at least the tip of the transfer device. The preferred embodiment of transfer device guide 46 has a diameter of 3/32 of an inch. Expansion slits 52 are small slits formed in upper surface 41 which radiate out from transfer device guide 41. There are four expansion slits in the preferred embodiment. The expansion slits are designed to expand slightly when a transfer device is inserted into and removed from cannula guide 41 to avoid undue friction between the transfer device and the transfer device guide and to prevent the transfer device guide from splitting. Similar to membrane 51, slits 52 should return substantially to their original position once the transfer device is removed, due to the elasticity of thermoplastic rubber, C-Flex or isoprene.

Figure 5:
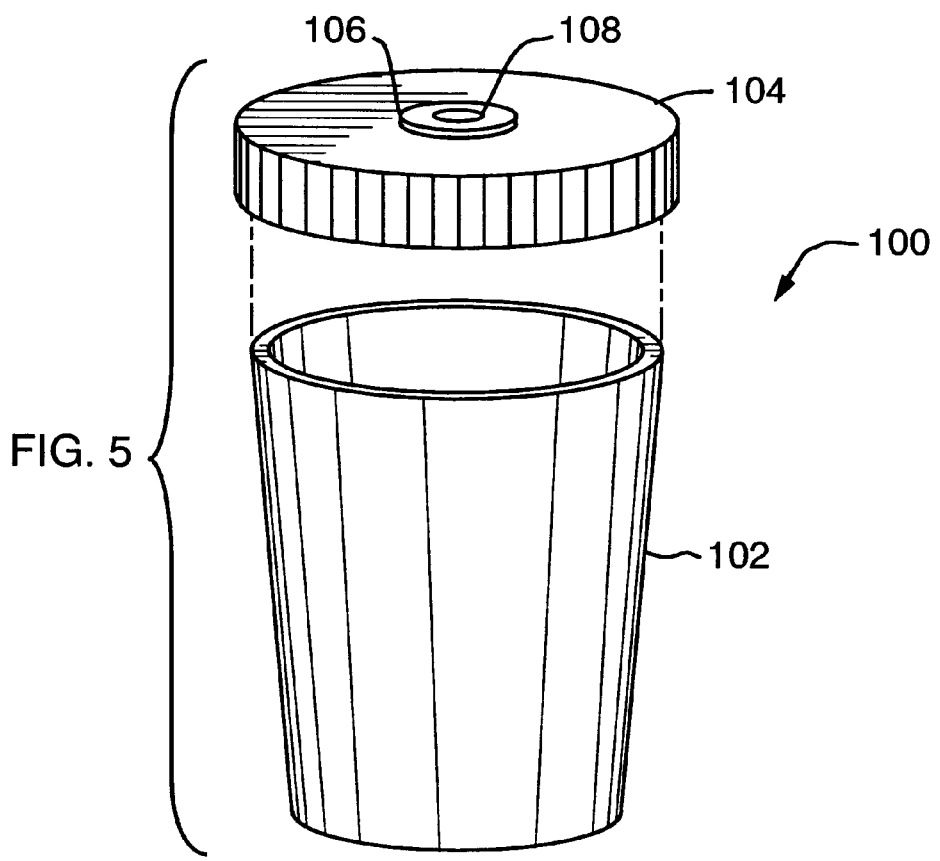
FIG. 5 is an exploded side view of another preferred embodiment of the specimen container of the invention.
Figure 6:
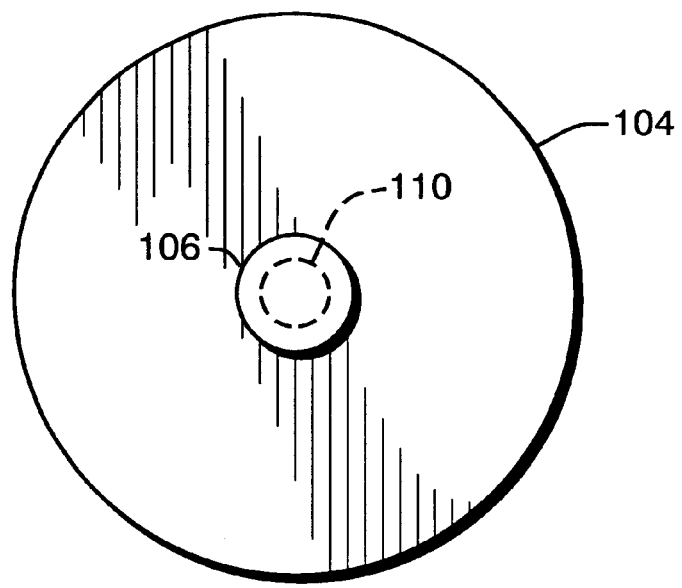
FIG. 6 is a top view of the preferred embodiment shown in FIG. 5.
Figure 9:
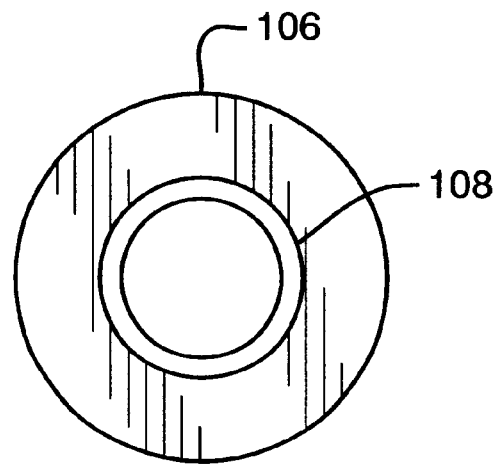
FIG. 9 is a top view of another preferred embodiment of the plug of the specimen container of the invention.

Another preferred embodiment of the specimen container of the invention, generally referred to as container 100, is shown in FIGS. 5 and 6. Container 100 comprises receptacle 102, lid 104 and plug 106. Unlike bore 25 described above as off center of lid 14, bore 110 and plug 106 are centered in lid 104. Plug 106 is substantially similar to plug 38 of container 10 except that plug 106 is substantially solid across its top surface. As shown in FIGS. 5 and 9, plug 106 could be provided with annular ridge 108 having an inner diameter which corresponds approximately to the inner diameter of bore 110 to facilitate insertion of a transfer device into and through bore 110.

Figure 7:
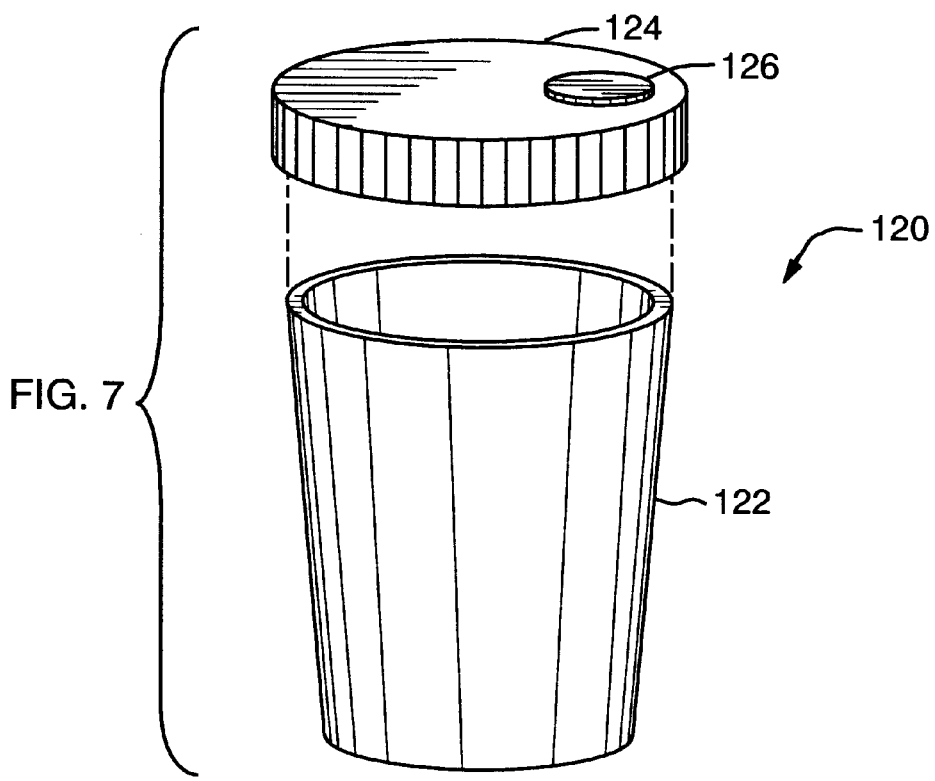
FIG. 7 is an exploded side view of yet another preferred embodiment of the specimen container of the invention.
Figure 8:
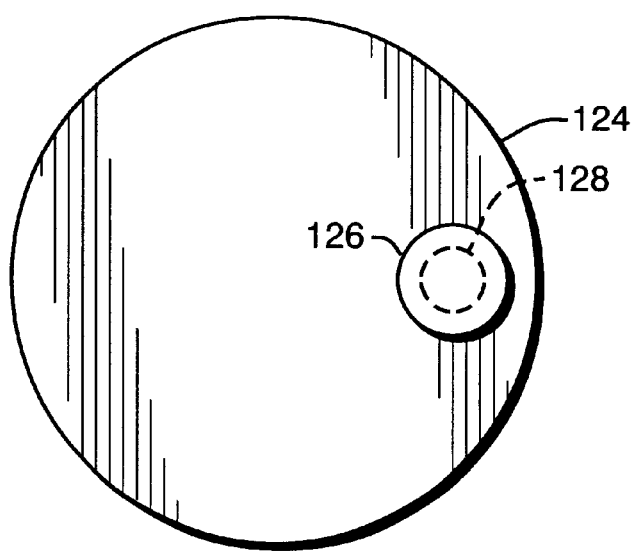
FIG. 8 is a top view of the preferred embodiment shown in FIG. 7.

Another preferred embodiment of the specimen container is shown in FIG. 7 and 8, generally referred to as container 122. Similar to container 100, container 122 comprises a receptacle 122, lid 124, bore 128 and plug 126, however bore 128 and plug 126 are off center of lid 124.

Figure 11A:
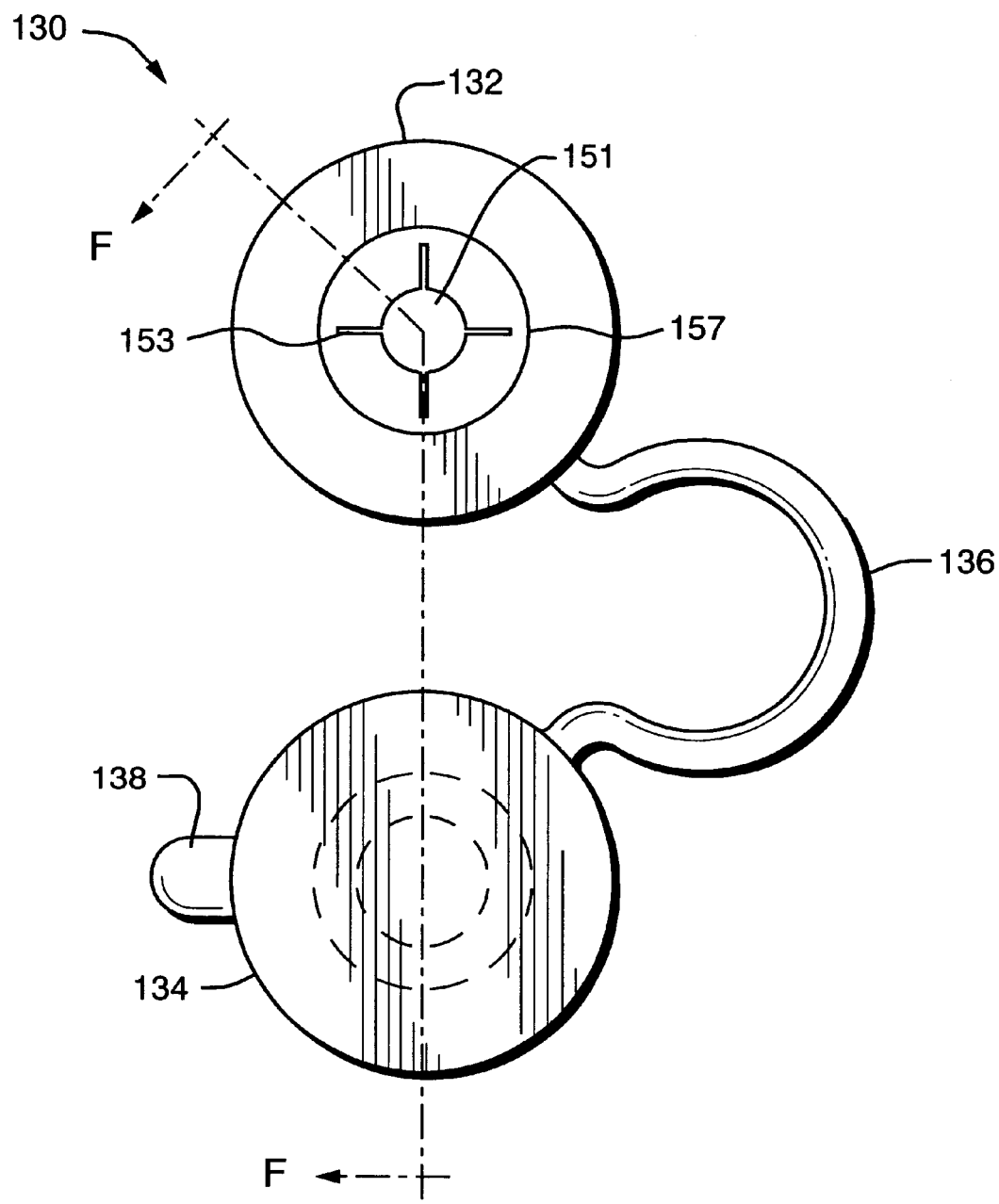
FIG. 11A is a top view of another preferred embodiment of the plug and plug cover of the specimen container of the invention.
Figure 11B:
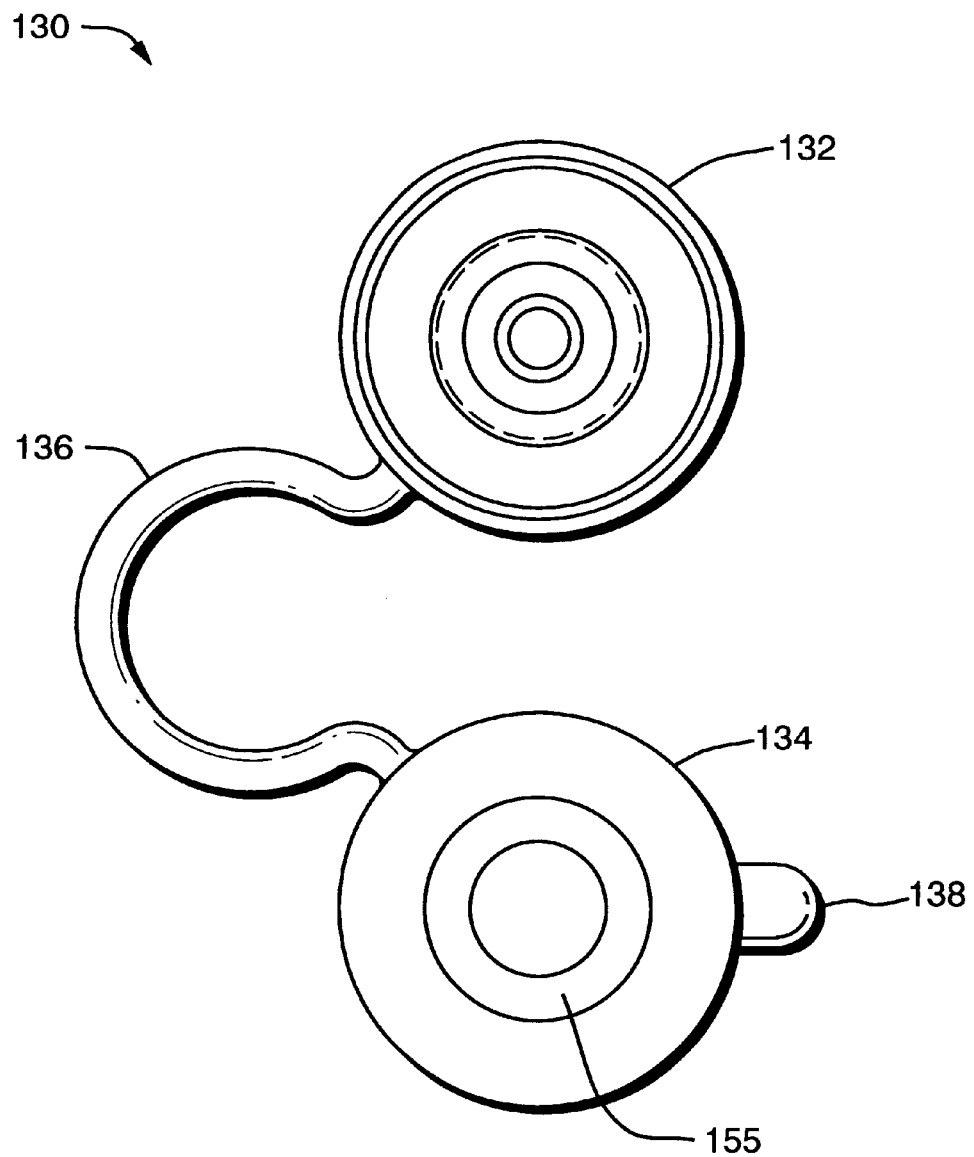
FIG. 11B is a bottom view of the plug and plug cover shown in FIG. 11A.

Another preferred embodiment of the plug and plug cover of the specimen container of the invention are shown in FIGS. 11A and 11B and generally referred to as unitary member 130. Unitary member 130 comprises plug 132 and plug cover 134 which are connected to each other by flexible cord 136. Plug cover 134 is provided with a thumb notch 138 which extends beyond the periphery of plug cover 134 to enable the user to lift plug cover 134 by pushing upwards from the bottom of notch 138 with the user's thumb or finger. Similar to plug 38, plug 132 is adapted for use with receptacle 10 and lid 14 having bore 25. Plug 132 is deformable so that the plug can be inserted into bore 25 for quick and easy assembly. Plug 132 has a larger upper shoulder 133 and a smaller lower shoulder 135. When plug 132 is inserted into bore 25, shoulder 133 is seated on the top surface of lid 14 and shoulder 135 is seated on the bottom edge of bore 25. Shoulder 135 preferably has a lip 137 which slightly wraps around the bottom edge of bore 25 to prevent plug 132 from being pulled up through bore 25 as the end of a cannula is pulled out through plug 132. Plug 132 has a slightly elongate portion 139 between shoulders 133 and 135 to accommodate the downward extension of sleeve-like bore 25. Elongate portion 139 of plug 38 should be about the same as the internal length of bore 25.

Figure 12:
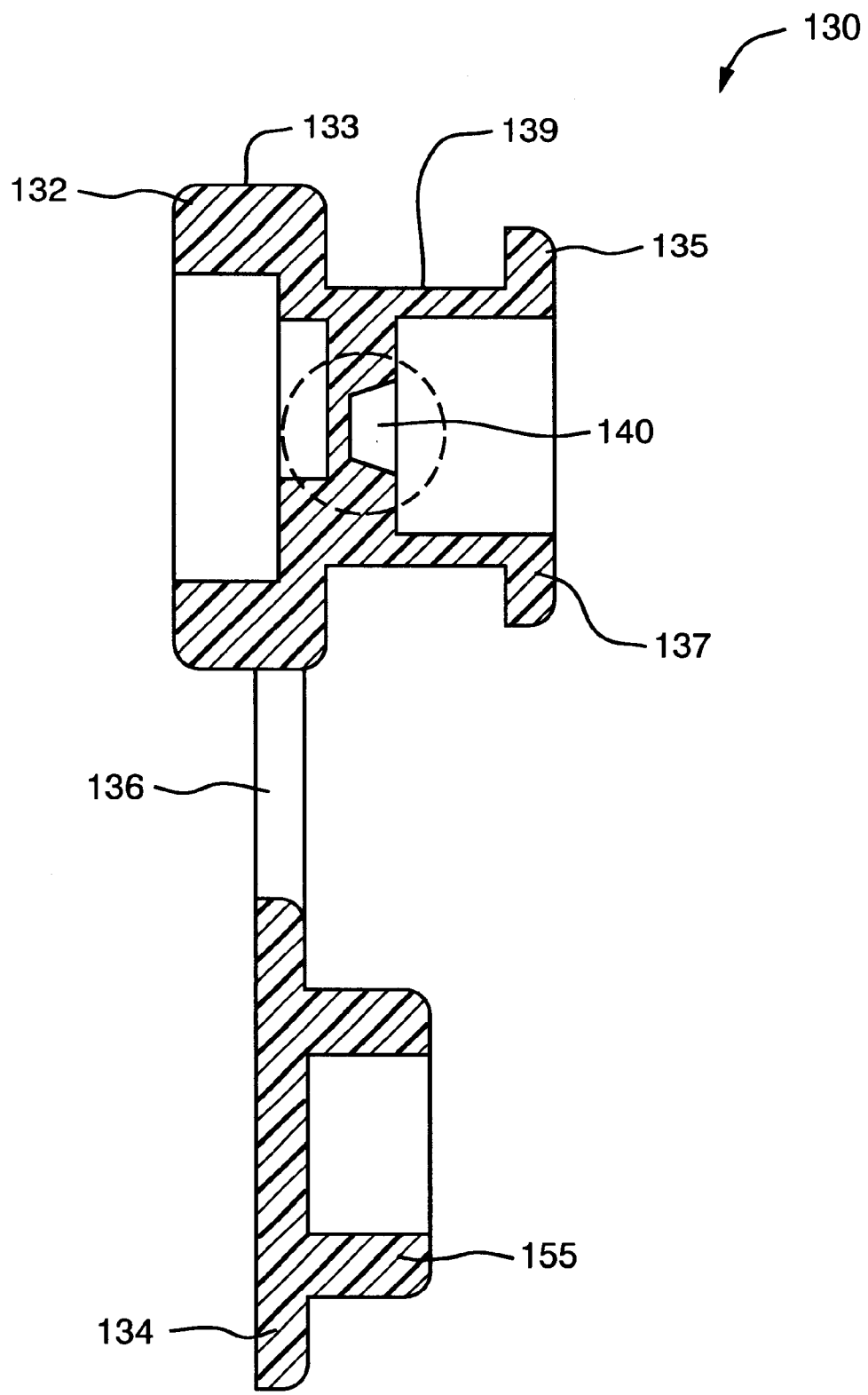
FIG. 12 is a cross-sectional view of the plug and plug cover shown in FIGS. 11A and 11B.
Figure 13:
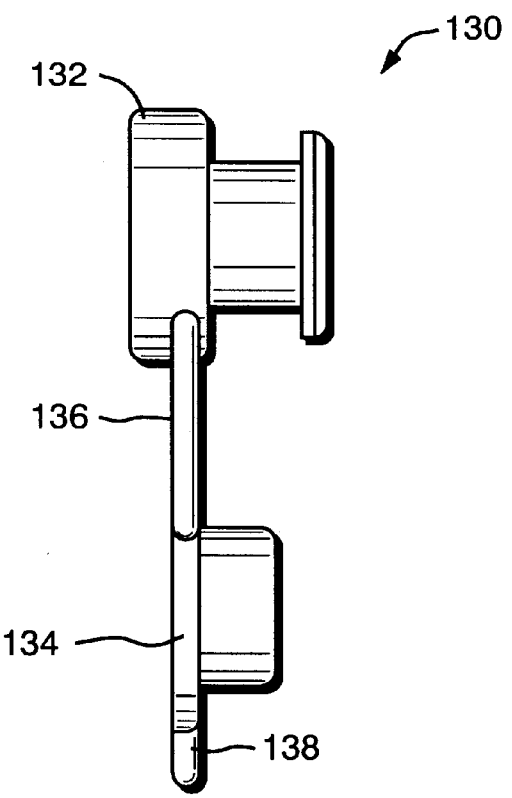
FIG. 13 is a side view of the plug and plug cover shown in FIGS. 11A and 11B.
Figure 14:
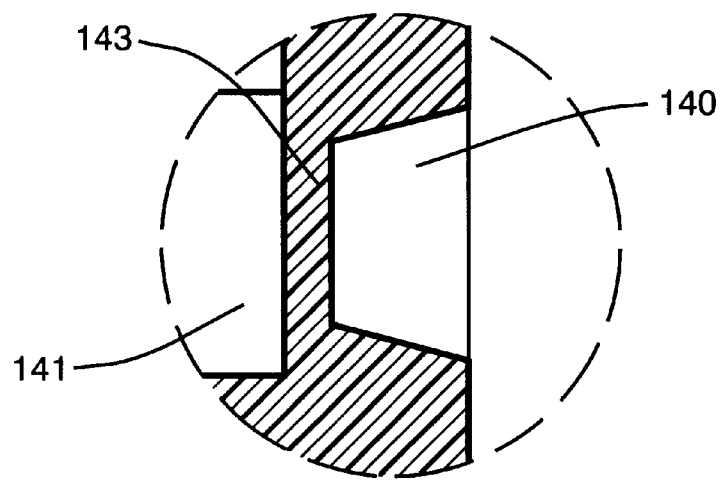
FIG. 14 is an enlarged view of Detail G shown in FIG. 12.
Figure 15B:
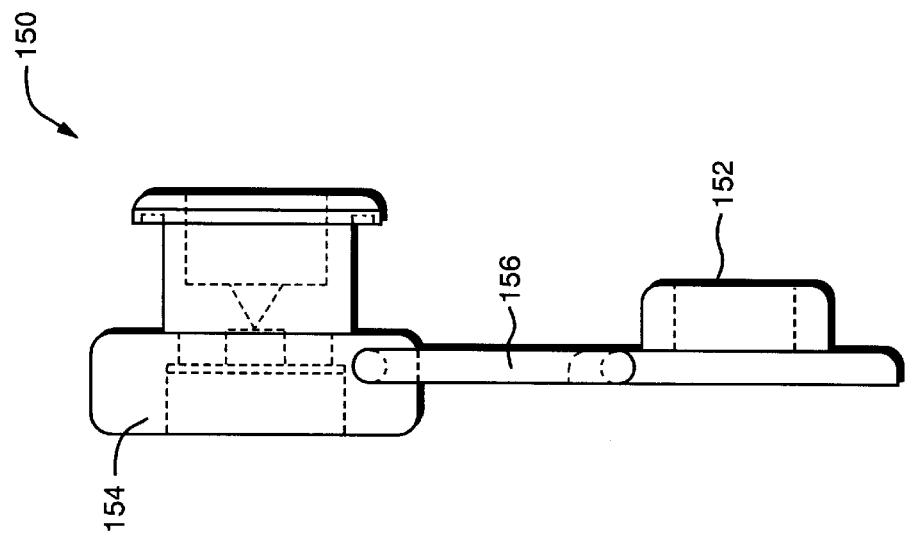
FIG. 15B is a side view of the plug and plug cover shown in FIG. 15A.
Figure 15A:
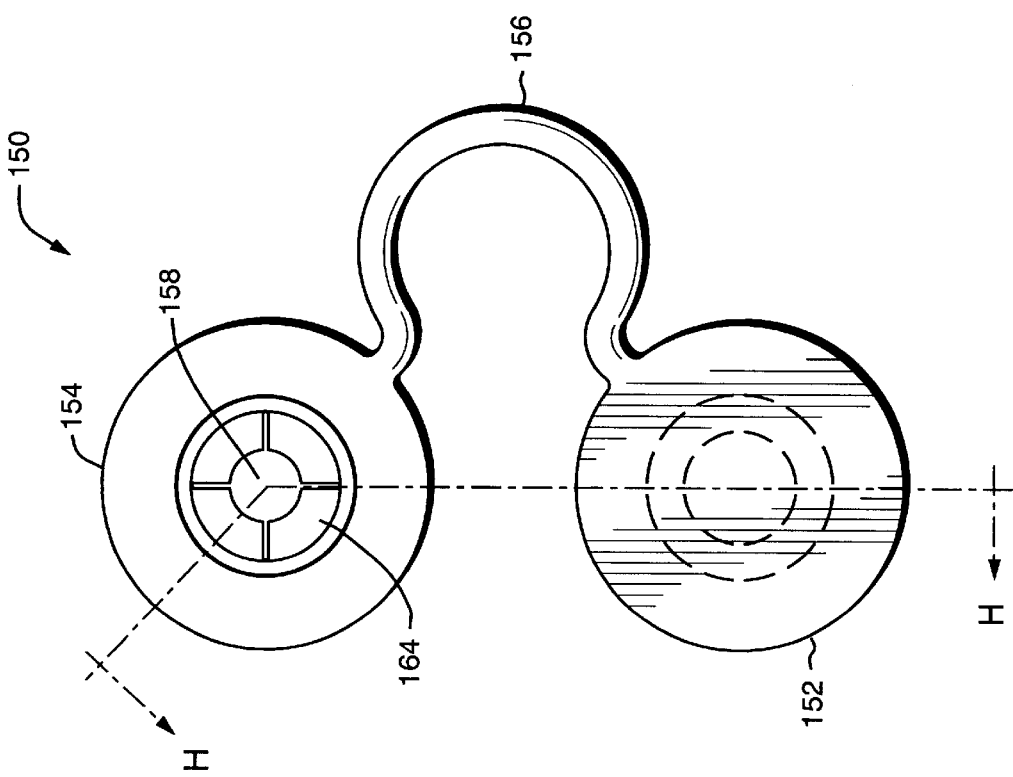
FIG. 15A is a top view of yet another preferred embodiment of the plug and plug cover of the specimen container of the invention.
Figure 16:
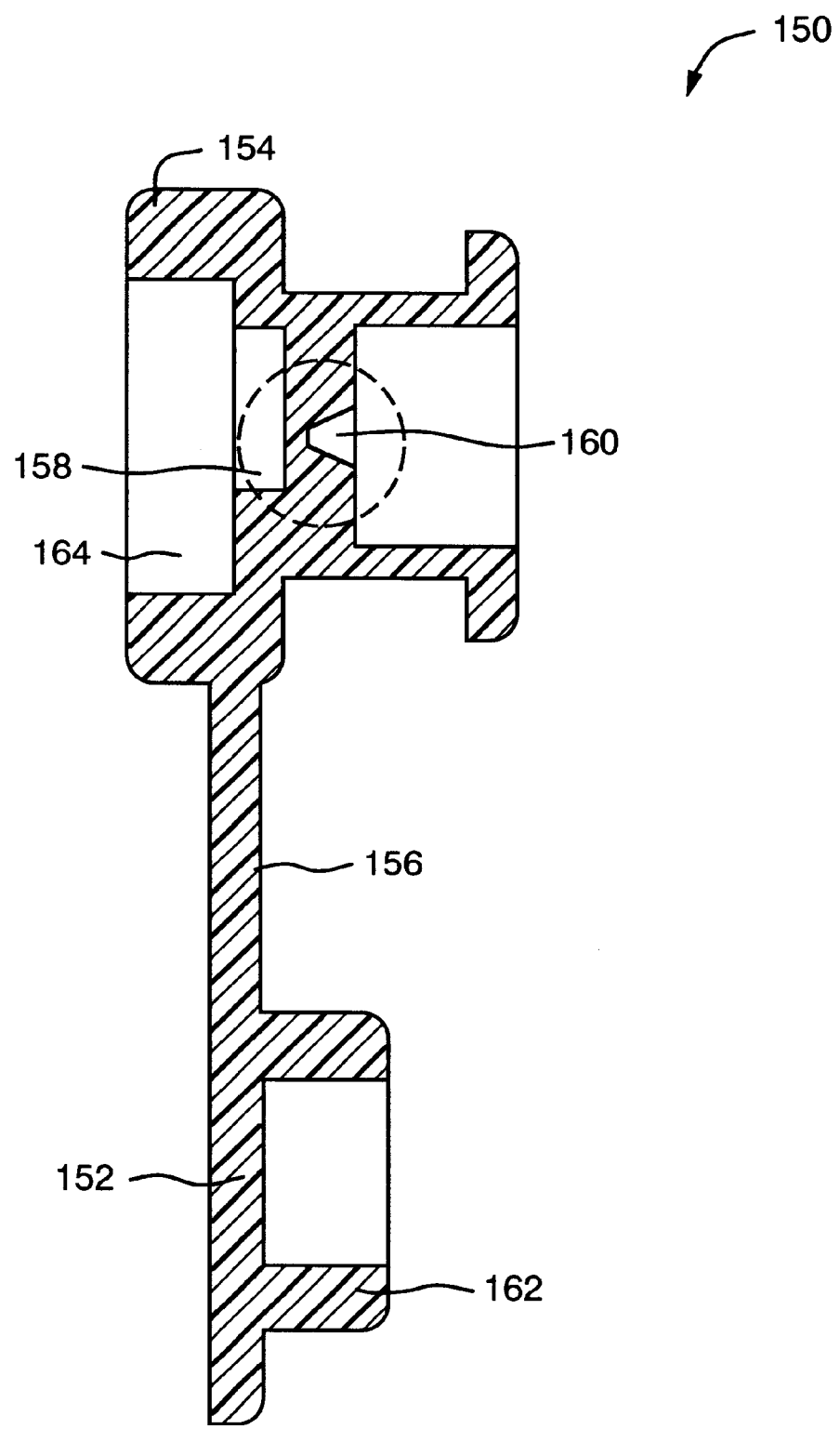
FIG. 16 is a cross-sectional view of the plug and plug cover shown in FIGS. 15A and 15B.
Figure 17:
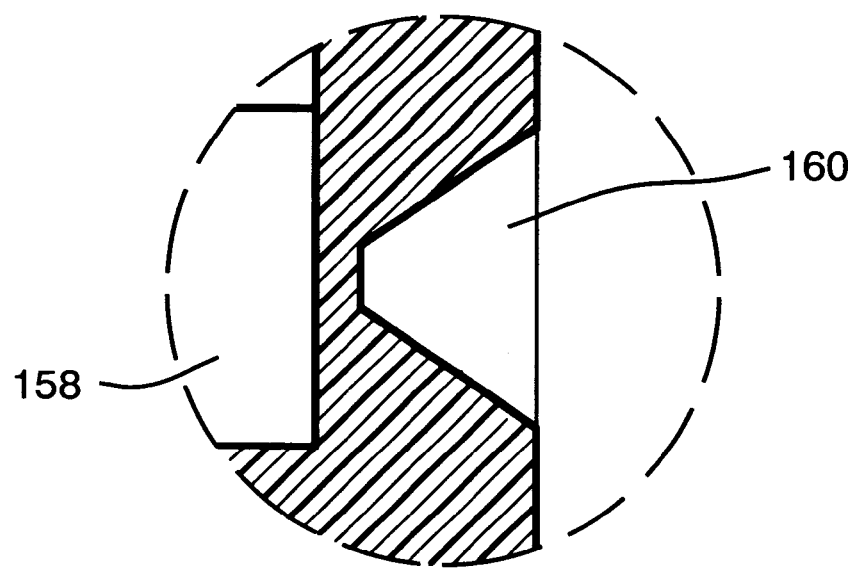
FIG. 17 is an enlarged view of Detail I shown in FIG. 16.

Plug 132 also has a central bore 141, however bore 141 does not extend the entire length of plug 132 as shown in FIGS. 12 and 14. A thin section at the upper end of elongate portion 139 is solid across its diameter to form self-sealing membrane 143. A small inverted notch 140 is provided in the bottom of membrane 143 to guide a material transfer device (not shown) back out through plug 132 and to channel any material back into receptacle 12 (not shown in FIGS. 12 and 14).

Upper surface of plug 132 is substantially solid across its face except for transfer device guide 151 and expansion slits 153. When unitary member 130 is in a closed position, cylindrical flange 155 is seated snugly within central bore 141. Annular sealing ridge 157 also extends upward from the upper surface so that when plug cover 134 is closed, sealing ridge 157 presses firmly against the bottom surface of cylindrical flange 155 of plug cover 134 to further inhibit leakage from container 10.

Figure 18:
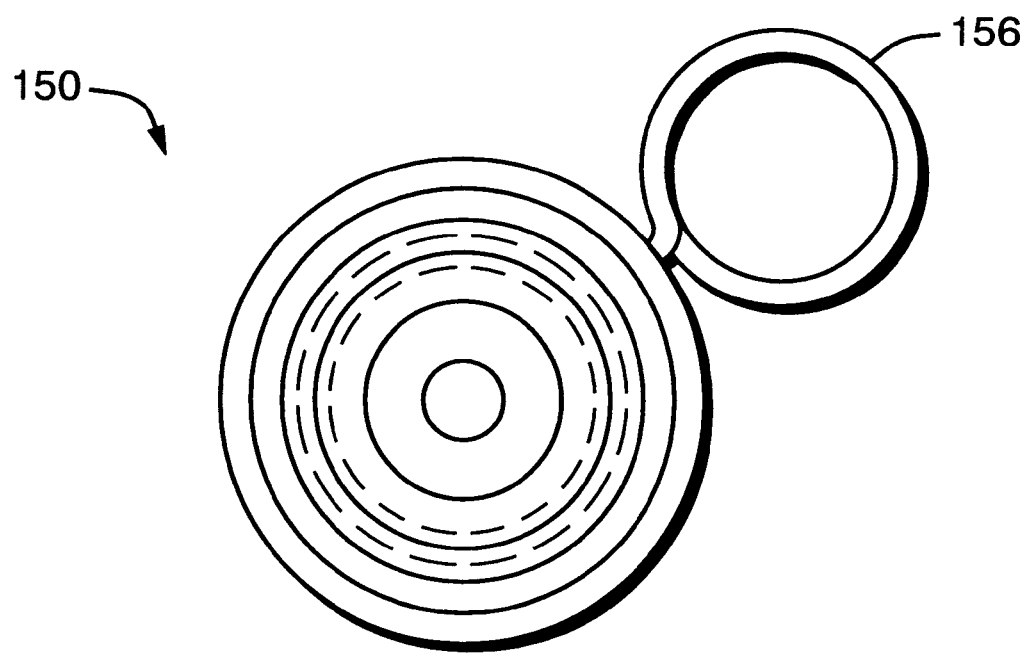
FIG. 18 is a top view of the plug and plug cover, shown in FIGS. 15A and 15B, in a closed position.
Figure 19G:
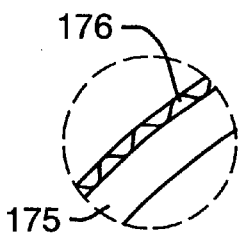
FIG. 19G is an enlarged view of Detail M of FIG. 19A.
Figure 19A:
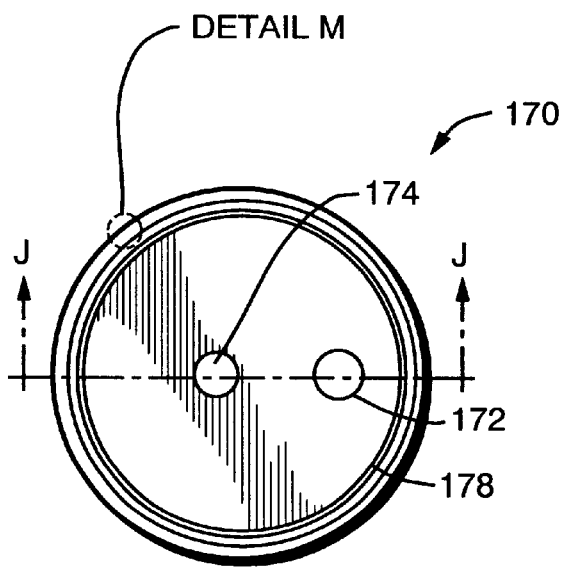
FIG. 19A is a top view of another preferred embodiment of the lid of the specimen cup of the invention.
Figure 19B:
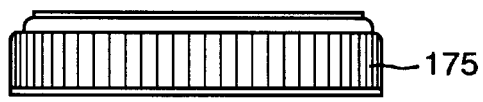
FIG. 19B is a side view of the lid shown in FIG. 19A.
Figure 19C:
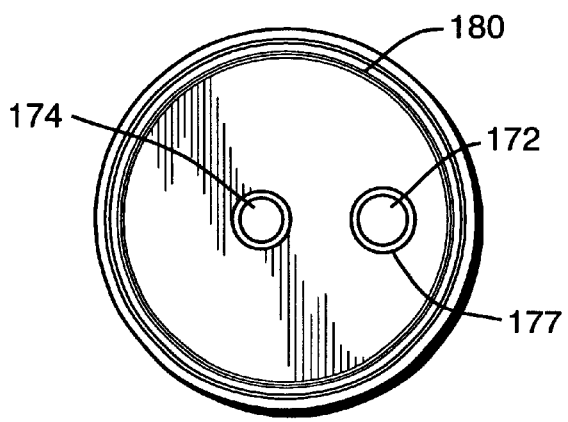
FIG. 19C is a bottom view of the lid shown in FIG. 19A.
Figure 19E:
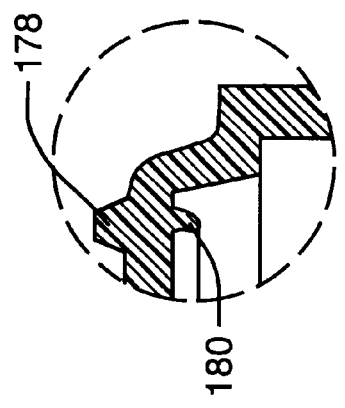
FIG. 19E is an enlarged view of Detail K of FIG. 19D.
Figure 19F:
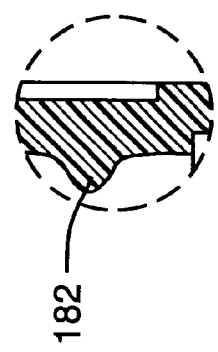
FIG. 19F is an enlarged view of Detail L of FIG. 19D.
Figure 19D:
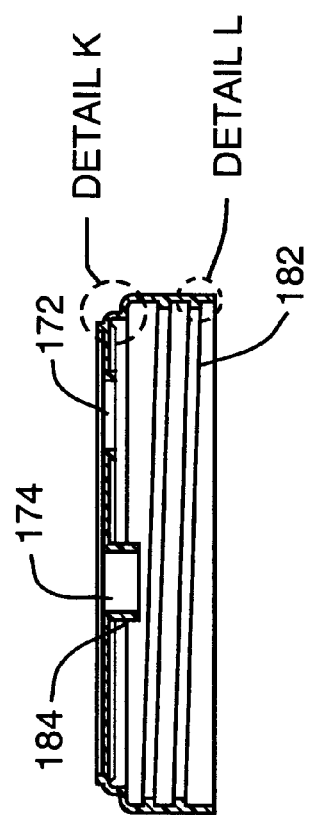
FIG. 19D is a cross-sectional view of the lid shown in FIG. 19A along line "J"—"J"

As shown in FIGS. 15A, 15B, 16, 17 and 18, unitary member 150 is yet another preferred embodiment of the plug and plug cover of the specimen container of the invention. Unitary member 150 generally comprises plug 154, plug cover 152 and connecting cord 156. Material transfer guide 158 is provided in plug 154. Unitary member 150 is similar in all respects to unitary member 130 except that unitary member 150 has a smaller inverted notch 160 and does not have a thumb notch extending past the peripheral edge of plug cover 152. When in a closed position, as shown in FIG. 18, unitary member 150 is opened by wedging a thumb or finger between the flexible periphery of plug cover 152 and the upper surface of plug 154 and lifting upwards to pull cylindrical flange 162 out of central bore 164.

FIGS. 19A–19G illustrate another preferred embodiment of a lid, generally referred to as lid 170, of the specimen container of the invention. In addition to a first bore 174, lid 170 is provided with a second bore 172. Bore 174 has a sleeve-like extension 184 (FIG. 19D) adapted to receive a plug (not shown) similar to any of the plugs described above, with or without a corresponding plug cover. Bore 172, although having a lower shoulder 177, typically does not have a sleeve-like extension as does bore 174. Bore 172 can be sealed with merely a plug cover similar to plug cover 152 of unitary member 150 described above. Lid 170 is also provided with external vertical ridges 176 around the outside of cylindrical wall 175. Lid 170 also is provided with annular ring 178 on the top outside surface of the lid and annular ring 180 on the top inside surface of the lid. Lid 170 may be attached to the above described receptacle, such as receptacle 12, by threads 182 on the inside surface of cylindrical wall 175. The second bore is adapted to allow a material transfer device, inoculation or sterile loop, pipet or a syringe without an attachment to be at least partially inserted into the specimen container.

Figure 20:
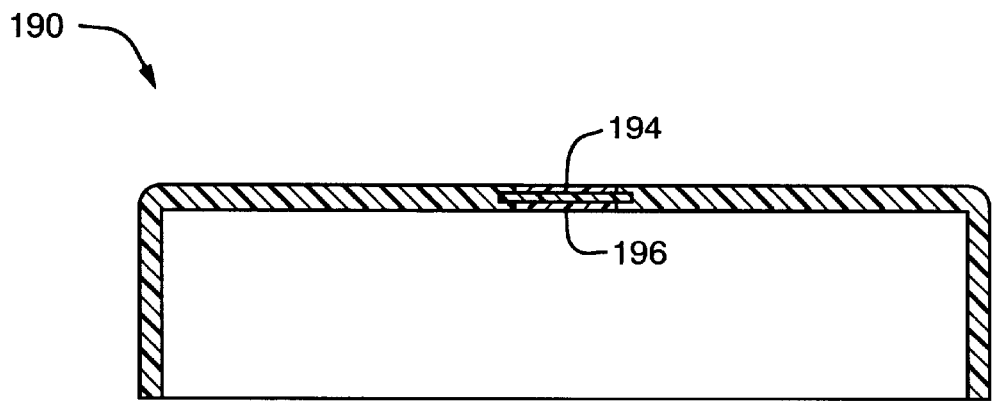
FIG. 20 is a cross-sectional view of yet another preferred embodiment of the lid of the specimen cup of the invention.
Figure 21:
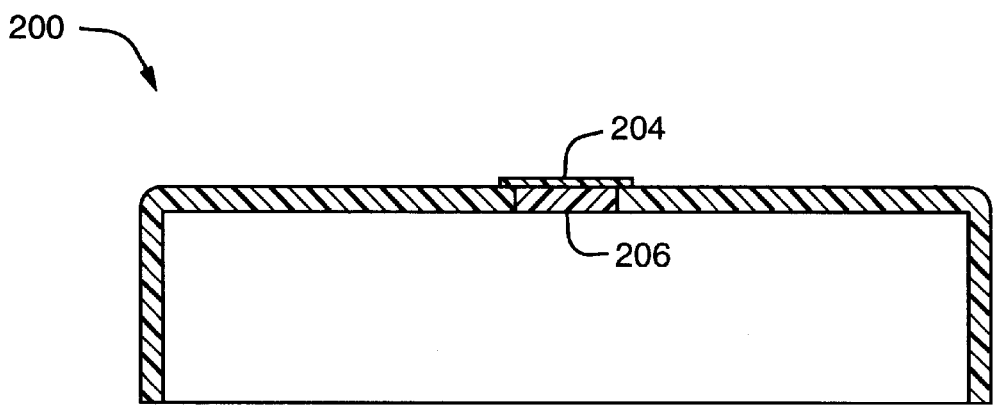
FIG. 21 is a cross-sectional view of yet another preferred embodiment of the lid of the specimen cup of the invention.

FIGS. 20 and 21 illustrate yet another preferred embodiment of the lid of the specimen cup of the invention. Lid 190 is provided with a single central bore 196 and membrane 194. Membrane 194 is molded into the top of lid 190 through a method known in the art as insertion molding. Lid 200 is similarly provided with a single central bore 206, however, membrane 204 is fixed to the top of lid 200 using an adhesive so that membrane 204 completely covers and seals the top opening of bore 206.

Figure 22:
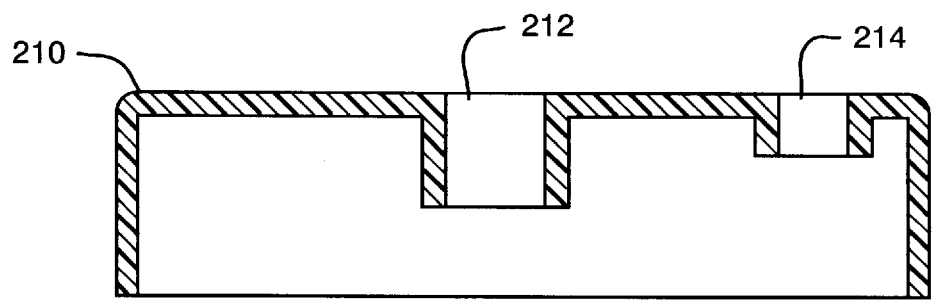
FIG. 22 is a cross-section view of yet another preferred embodiment of the lid of the invention.
Figure 23:
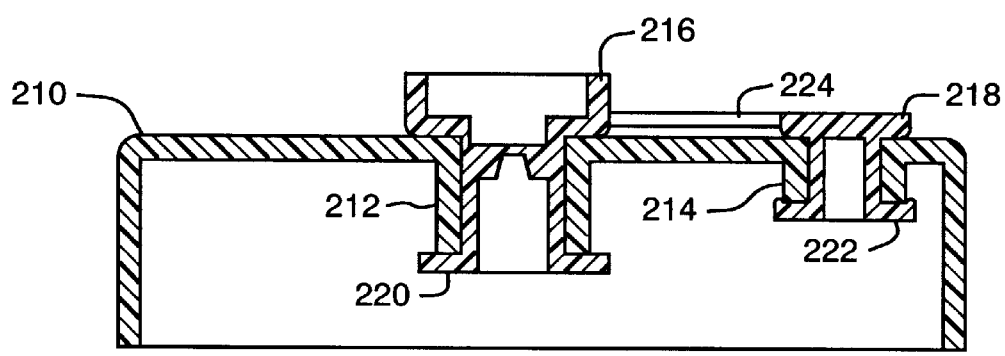
FIG. 23 is a cross-sectional view of yet another preferred embodiment of the plug cover of the invention inserted into the lid of FIG. 22.
Figure 24A:
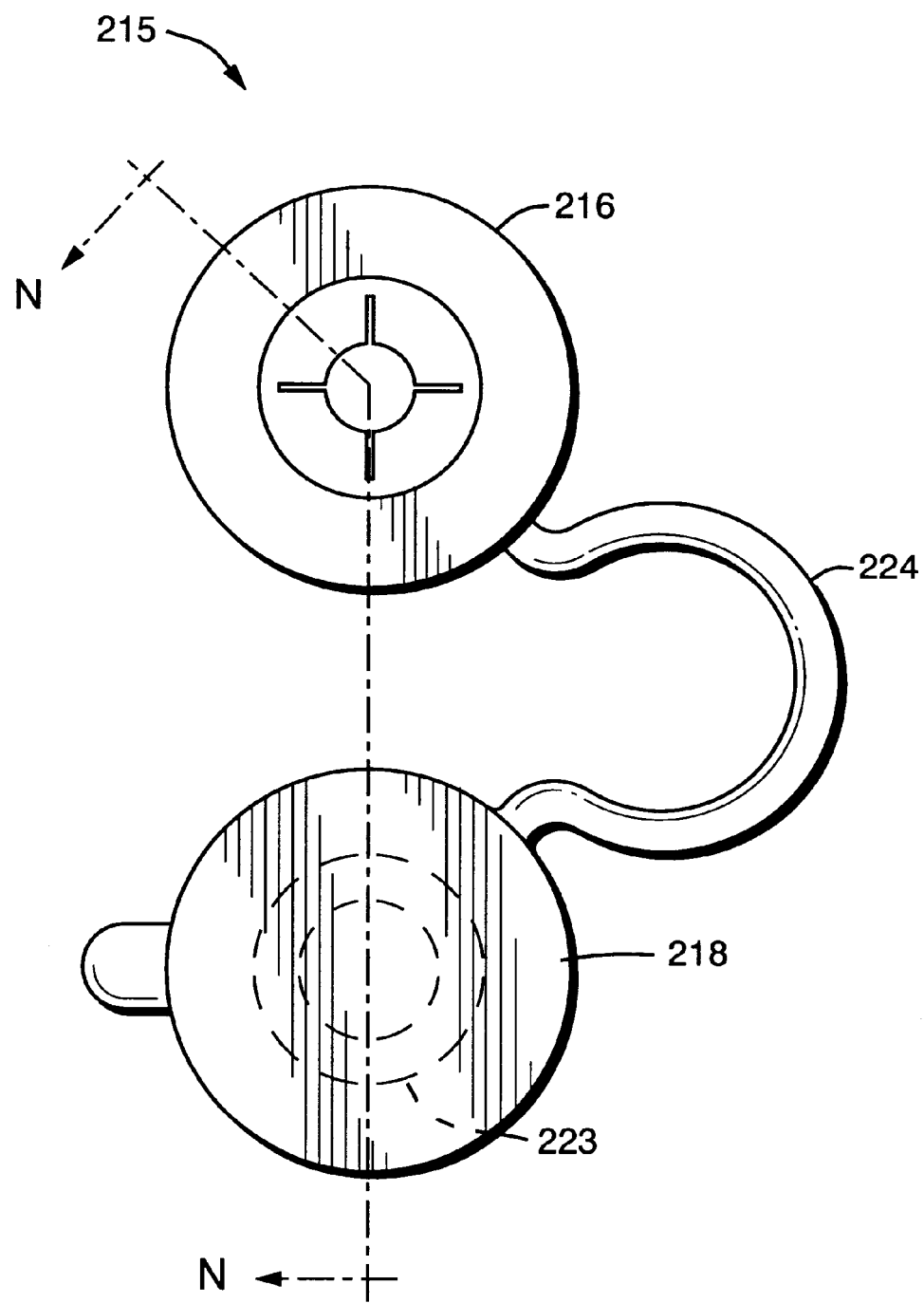
FIG. 24A is a top view of the plug cover shown in FIG. 23.
Figure 24B:
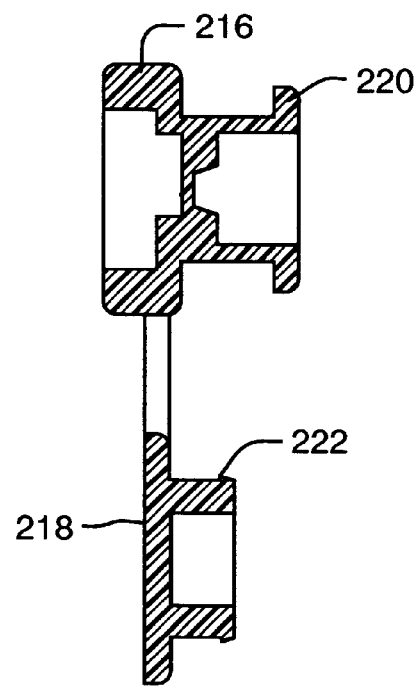
FIG. 24B is a cross-sectional view of the plug cover shown in FIG. 23.
Figure 24C:
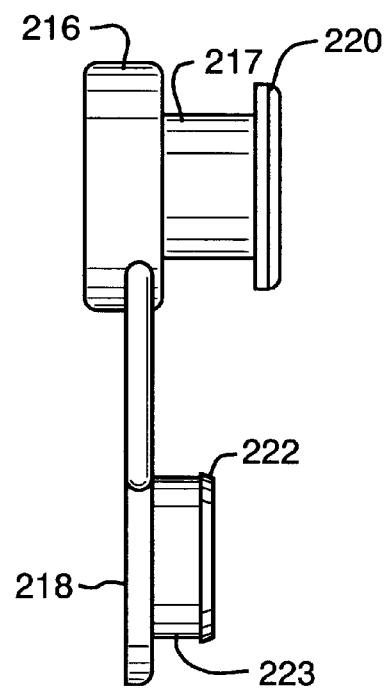
FIG. 24C is a side view of the plug cover shown in FIG. 23.

FIG. 22 is another preferred embodiment of the lid, generally referred to as lid 210, which is similar to lid 170, having two bores 212 and 214 through the top of lid 210. Both bores comprise a conduit which extends downward from the top of lid 210. The conduit of bore 212 is somewhat longer than the conduit of bore 214. Bores 212 and 214 may be sealed using unitary dual plug 215 (FIGS. 24A–C) as shown in FIG. 23. Unitary dual plug 215 comprising a first plug 216 provided with an elongate portion 217 adapted to fit into the conduit of bore 212 and shoulder 220 adapted to rest on the lower surface of bore 212's conduit. Bore 214 is sealed by inserting second plug 218 provided with slightly elongate portion 223 adapted to fit into the conduit of bore 214 and shoulder 222 adapted to rest on the lower surface of bore 214's conduit. First plug 216 and second plug 218 are connected together by flexible cord 224, all of which are preferably a molded unitary member.

Figure 25:
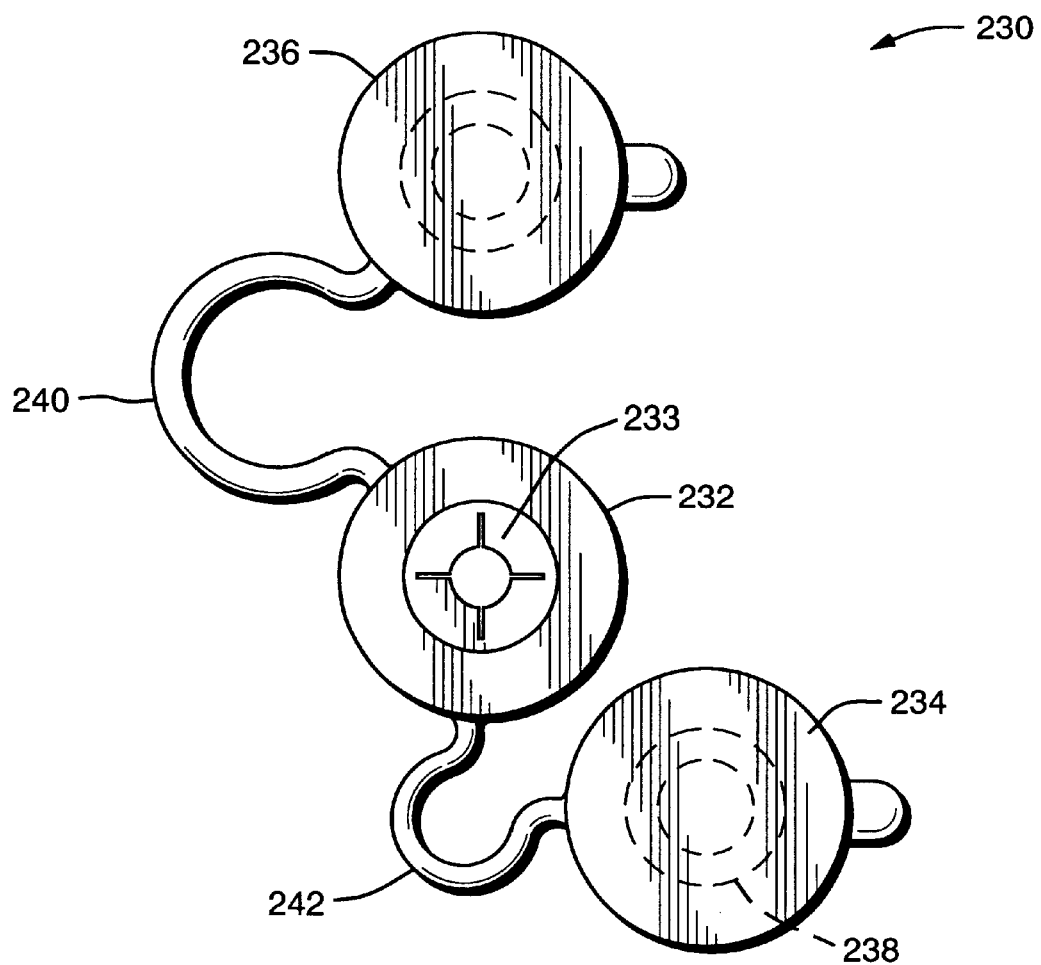
FIG. 25 is a top view of yet another preferred embodiment of the plug of the invention.
Figure 26:
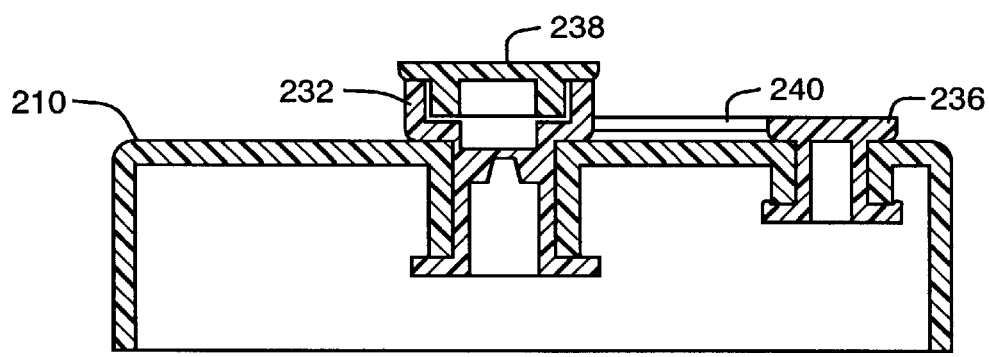
FIG. 26 is a cross-sectional view of the plug shown in FIG. 25 inserted into the lid of FIG. 22.

FIG. 25 is another preferred embodiment of a unitary dual plug and single plug cover of the invention, generally referred to as plug 230. Plug 230 is adapted for use with lid 210 to seal both bore 212 and bore 214. Plug 230 comprises a first plug 232 for sealing bore 212 and second plug 238 for sealing bore 214. Plugs 232 and 238 are connected together by flexible cord 240. Plug 230 is additionally provided with plug cover 234 which is adapted to cover first plug 232 as shown in FIG. 26. Similar to plug 154, first plug 232 is provided with central bore 233 and similar to plug cover 152, plug cover 234 is provided with cylindrical flange 238 adapted to be seated in central bore 233. Plug cover 234 is connected to first plug 232 by flexible cord 242. Plug 230 is preferably a molded unitary member.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. A lid, for a specimen container having an opening, adapted to enable a user to inject or withdraw materials into or out of said container using a material transfer device with minimal risk of spills or leaks, comprising;

a cover portion comprising:
        a means to seal said opening and at least a first bore and a second bore therethrough, and
        a top surface and a bottom surface and a conduit extending downward from said bottom surface of said lid, through which said first bore extends and which comprises a distal lower lip;

a first plug, which is seated in said first bore of said lid comprising:
        a membrane capable of being penetrated with a material transfer device and which self-reseals to prevent leakage from said container; and a second plug which is seated in said second bore.

2. The lid for a specimen container of claim 1, further comprising, at first plug cover which covers said first plug; and
    a second plug cover which covers said second plug.

3. The lid for a specimen container of claim 2, wherein said first plug and said first plug cover are connected to each other by a flexible cord.

4. The lid for a specimen container of claim 3, wherein said second plug and said first plug are connected to each other by a flexible cord.

5. The lid for a specimen container of claim 1, further comprising, a first plug cover which covers said first plug.

6. The lid for a specimen container of claim 5, wherein said first and second plug and said first plug cover are a molded unitary plug member comprising a flexible cord connecting said first plug to said first plug cover.

7. The lid for a specimen container of claim 6, wherein said molded unitary plug member is molded from thermoplastic rubber.

8. The lid for a specimen container of claim 1, wherein said first plug further comprises:

an upper and lower shoulder, wherein said upper shoulder is seated on said top surface of said cover portion and said lower shoulder is seated on said lower lip of said conduit, a material transfer device guide having a perimeter and an outer diameter and centered in said conduit, and a plurality of expandable slits which radiate outward from said perimeter of said material transfer device guide and which enable said outer diameter of said guide to flexibly expand in order to accommodate material transfer devices having varying outer diameters.

9. The lid for a specimen container of claim 1, wherein said first and second plugs are a molded unitary plug member comprising a flexible cord connecting said first plug to said second plug.

* * * * *